(12) United States Patent
Hong et al.

(10) Patent No.: US 11,449,790 B2
(45) Date of Patent: Sep. 20, 2022

(54) ARTIFICIAL INTELLIGENCE DEVICE AND METHOD FOR EXECUTING AN OPERATION BASED ON PREDICTED BIOMETRIC STATE OF A USER

(71) Applicant: LG ELECTRONICS INC., Seoul (KR)

(72) Inventors: Gyuseog Hong, Seoul (KR); Taehwan Kim, Seoul (KR); Byunghun Choi, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 804 days.

(21) Appl. No.: 16/168,415

(22) Filed: Oct. 23, 2018

(65) Prior Publication Data
US 2020/0089653 A1    Mar. 19, 2020

(30) Foreign Application Priority Data
Sep. 19, 2018    (KR) .................. 10-2018-0112480

(51) Int. Cl.
*G06N 20/00*    (2019.01)
*G06N 3/04*    (2006.01)
(Continued)

(52) U.S. Cl.
CPC .......... *G06N 20/00* (2019.01); *A61B 5/0008* (2013.01); *G06N 3/0454* (2013.01); *G06N 3/0472* (2013.01); *G06N 20/20* (2019.01)

(58) Field of Classification Search
None
See application file for complete search history.

(56) References Cited

U.S. PATENT DOCUMENTS 8,527,276 B1 *  9/2013  Senior .................... G06N 3/084
                                                                704/259
2013/0024414 A1  1/2013  Herzog
(Continued)

FOREIGN PATENT DOCUMENTS

JP    2018-512086 A    5/2018
KR    10-2017-0053692 A    5/2017

OTHER PUBLICATIONS

Zhu et al. "Active Learning From Stream Data Using Optimal Weight Classifier Ensemble." 2010. IEEE Transactions on Systems, Man, and Cybernetics, Part B (Cybernetics). vol. 40, Issue: 6, pp. 1607-1621 (Year: 2010).*

(Continued)

*Primary Examiner* — Abdullah Al Kawsar
*Assistant Examiner* — Asher H. Jablon
(74) *Attorney, Agent, or Firm* — Birch, Stewart, Kolasch & Birch, LLP

(57) ABSTRACT

A computer-implemented method for controlling a device based on an ensemble model can include receiving sensing information associated with a user's biometric state; inputting first sensing information to a first model, determining a first uncertainty of the first model, and generating a first weight value for weighting a first result value; inputting second sensing information into a second model, determining a second uncertainty of the second model, and generating a second weight value for weighting a second result value; generating a final result value based on combining the first result value weighted by the first weight value and the second result value weighted by the second weight value; generating a predicted biometric state of the user based on the final result value; and executing an operation of the device based on the predicted biometric state.

10 Claims, 11 Drawing Sheets

(51) Int. Cl.
*G06N 20/20* (2019.01)
*A61B 5/00* (2006.01)

(56) References Cited

U.S. PATENT DOCUMENTS

| | | | |
|---|---|---|---|
| 2013/0339280 A1 | 12/2013 | Hunzinger et al. | |
| 2014/0278139 A1* | 9/2014 | Hong | A61B 5/1118 702/19 |
| 2015/0134413 A1* | 5/2015 | Deshpande | G06Q 30/0202 705/7.31 |
| 2016/0321523 A1* | 11/2016 | Sen | G06T 15/06 |
| 2017/0249559 A1 | 8/2017 | Herzog | |
| 2018/0046942 A1 | 2/2018 | Conroy et al. | |
| 2018/0168485 A1* | 6/2018 | Chen | G08B 21/22 |
| 2018/0203978 A1 | 7/2018 | Basu et al. | |
| 2019/0130256 A1* | 5/2019 | Ghahramani | G06N 3/0472 |
| 2020/0250475 A1* | 8/2020 | Ikeda | G06F 11/07 |

OTHER PUBLICATIONS

Sebastian Raschka. "EnsembleVoteClassifier." Mar. 1, 2016. Published on GitHub Pages and retrieved with Wayback Machine. https://web.archive.org/web/20160301025548/http:/rasbt.github.io/mlxtend/user_guide/classifier/EnsembleVoteClassifier/ (Year: 2016).*

Jimenez, Daniel, "Dynamically Weighted Ensemble Neural Networks for Classification," Proceedings of the 1998 International Joint Conference on Neural Networks (IJCNN), 4 pages, accessed at URL https://people.engr.tamu.edu/djimenez/taco/pubs.html (Year: 1998).*

Chen et al. "Deep Feature Learning for Medical Image Analysis with Convolutional Autoencoder Neural Network." Jun. 20, 2017. IEEE Transactions on Big Data. 10 Pages. (Year: 2017).*

Malhotra et al., "LSTM-based Encoder-Decoder for Multi-sensor Anomaly Detection", 2016, arXiv:1607.00148v2 [cs.AI], 5 pages (Year: 2016).*

* cited by examiner

ARTIFICIAL INTELLIGENCE DEVICE AND METHOD FOR EXECUTING AN OPERATION BASED ON PREDICTED BIOMETRIC STATE OF A USER

CROSS-REFERENCE TO RELATED APPLICATIONS

This application claims priority to Korean Patent Application No. 10-2018-0112480 filed on Sep. 19, 2018 in Korea, the entire contents of which is hereby incorporated by reference in its entirety.

BACKGROUND

Field of the Invention

The present invention relates to an artificial intelligence device which controls weight values of result values of a plurality of models in an ensemble model which combines the result values of the plurality of models to output a final result value.

Discussion of the Related Art

Artificial intelligence (AI) is in the field of information technology and computer engineering for researching a method of allowing a computer to perform thinking, learning, and self-development based on intelligence of humans, and denotes that computers imitate intelligent behaviors of humans.

Moreover, AI is indirectly and directly much associated with the field of computer engineering without existing itself. Particularly, an AI component is applied to various fields of information technology recently, and an attempt to solve problems in the fields is being very actively made.

An ensemble learning method is a method which uses a number of learning algorithms for obtaining prediction performance better than a case where a learning algorithm is separately used in machine learning.

Moreover, an ensemble model uses the ensemble learning method and denotes a final prediction model which is obtained by combining a plurality of prediction models differently learned based on various learning algorithms and various data.

When data is input, each of the plurality of prediction models outputs a result value, and the ensemble model combines the result values output from the plurality of prediction models to output a final result value.

A related art ensemble model assigns the same weight value to result values output from a plurality of prediction models to output a final result value.

When noise or previously unlearned data is input to a specific prediction model of the plurality of prediction models, the uncertainty of a result value of the specific prediction model increases. That is, the uncertainties of result values output from the plurality of prediction models may differ.

However, in the related art ensemble model, despite an uncertainty difference, since the same weight value is assigned to the result values output from the plurality of prediction models, the uncertainty of the final result value is reduced.

SUMMARY

An aspect of the present invention is directed to providing an artificial intelligence (AI) device which controls weight values of result values of a plurality of models in an ensemble model which combines the result values of the plurality of models to output a final result value.

To achieve these and other advantages and in accordance with the purpose of the disclosure, as embodied and broadly described herein, there is provided computer-implemented method for inputting sensing information to an ensemble model to obtain a final result value, the computer-implemented method including obtaining pieces of sensing information associated with a biometric state, inputting the pieces of sensing information to an ensemble model which includes a plurality of models and combines result values output from the plurality of models to output the final result value, inputting first sensing information of the pieces of sensing information to a first model of the plurality of models, obtaining a first uncertainty of the first model by using at least one of an input value and an output value of the first model, and determining a first weight value of a first result value of the first model by using the first uncertainty, inputting second sensing information of the pieces of sensing information to a second model of the plurality of models, obtaining a second uncertainty of the second model by using at least one of an input value and an output value of the second model, and determining a second weight value of a second result value of the second model by using the second uncertainty, combining, by using the ensemble model, the first result value to which the first weight value is applied and a second result value to which the second weight value is applied to obtain the final result value, and performing an operation corresponding to the biometric state, based on the final result value.

Further scope of applicability of the present invention will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

BRIEF DESCRIPTION OF THE DRAWINGS

The accompanying drawings, which are included to provide a further understanding of the disclosure and are incorporated in and constitute a part of this application, illustrate embodiments of the disclosure and together with the description serve to explain the principle of the disclosure. In the drawings.

DETAILED DESCRIPTION OF THE DISCLOSURE

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context. Terms such as "include" or "has" are used herein and should be understood that they are intended to indicate an existence of several components, functions or steps, disclosed in the specification, and it is also understood that greater or fewer components, functions, or steps may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart watches, smart glasses, head mounted displays (HMDs)), and the like.

By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, and the like.

Figure 1:
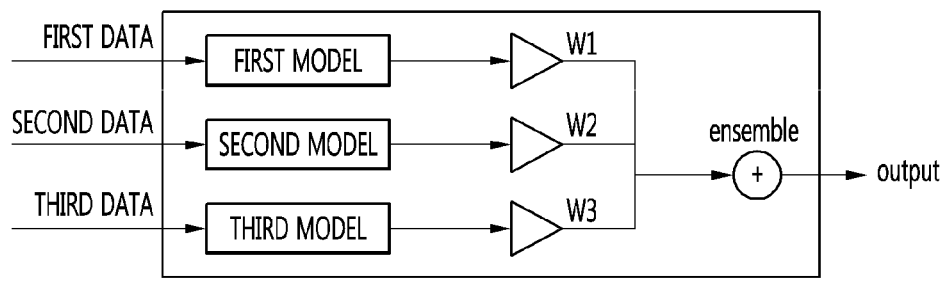
FIG. 1 is a diagram for describing a problem which occurs when the same weight value is assigned to result values of a plurality of models in a case of generating an ensemble model for obtaining information about a biometric state, according to an embodiment of the present invention.

FIG. 1 is a diagram for describing a problem which occurs when the same weight value is assigned to result values of a plurality of models in a case of generating an ensemble model for obtaining information about a biometric state, according to an embodiment of the present invention.

The ensemble model may include a first model which receives first data to output a first result value, a second model which receives second data to output a second result value, and a third model which receives third data to output a third result value.

Here, the ensemble model may be a model for predicting a biometric state of a user.

In a case where various features such as a motion, a physiological signal, and a sound of a user are combined and used, a biometric state of the user may be more accurately predicted.

Therefore, the ensemble model may combine result values of a plurality of models to output a final result value, thereby more accurately predicting the biometric state of the user.

The first data may be motion data obtained by sensing a motion of the user, and the first model may be a model for predicting a motion state of the user.

The second data may be biometric signal data obtained by sensing the physiological signal, such as a heart rate or a temperature, of the user, and the second model may be a model for predicting the biometric state of the user.

The third data may be sound data obtained by sensing a sound signal, such as snoring, of the user, and the third model may be a model for predicting a sound state of the user.

Each of the first model, the second model, and the third model may output a result value, based on data input thereto. Also, the ensemble model may apply the same weight value to the result values output from the first to third models to output a final result value.

Noise or unlearned data may be input to the ensemble model.

For example, when the first model is a model which predicts a motion state of a sleeping user on the basis of a motion of the user, data unassociated with a motion, performed in sleeping, of the user and data corresponding to a motion, such as waking up and going to a restroom, moving of a person next to the user, or moving of a surrounding object, of another person may be input to the first model.

As another example, when the second model is a model which predicts a physiological state of the user on the basis of the physiological signal of the user, data corresponding to a case where breathing or pulsation is abnormally measured due to a motion of the user may be input to the second model, and data corresponding to a case where a signal of a person next to the user is measured may be input to the second model.

As another example, when the third model is a model which predicts a sound state of the user on the basis of a sound of the user, noise of an ambient environment may be measured and may be input to the third model, and a changed sound when the user has a cold may be input to the third model.

An example, where a heart rate is abnormally measured due to a motion of the user and thus noise is included in the second data, will be described below.

When the second data including noise is received, the second model may output a right answer as high reliability. For example, an actual heart rate of the user may be 60 but may be abnormally measured as 90, and when a signal measured as 90 is input, the second model may output a right answer corresponding to 90. However, since the second model does not know the uncertainty of 90, the second model may output a right answer corresponding to 90 as high reliability.

Since a result value of the second model is inaccurate, the ensemble model, in a case where the ensemble model applies the same weight value to the result values of the first to third models to output a final result value, the final result value may be inaccurate.

That is, each of the first to third models may output a result value representing a case where a right answer is ensured or may output a result value representing a case where the right answer is not ensured, based on data input thereto. Here, a degree to which a result value output from each model is ensured as a right answer may be referred to as uncertainty.

When the ensemble model assigns the same weight value to an output value of the first model, an output value of the second model, and an output value of the third model regardless of uncertainty, an output value which is high in uncertainty and an output value which is low in uncertainty may be identically applied to a final result value. In this case, the reliability of the final result value of the ensemble model may be reduced.

Figure 2:
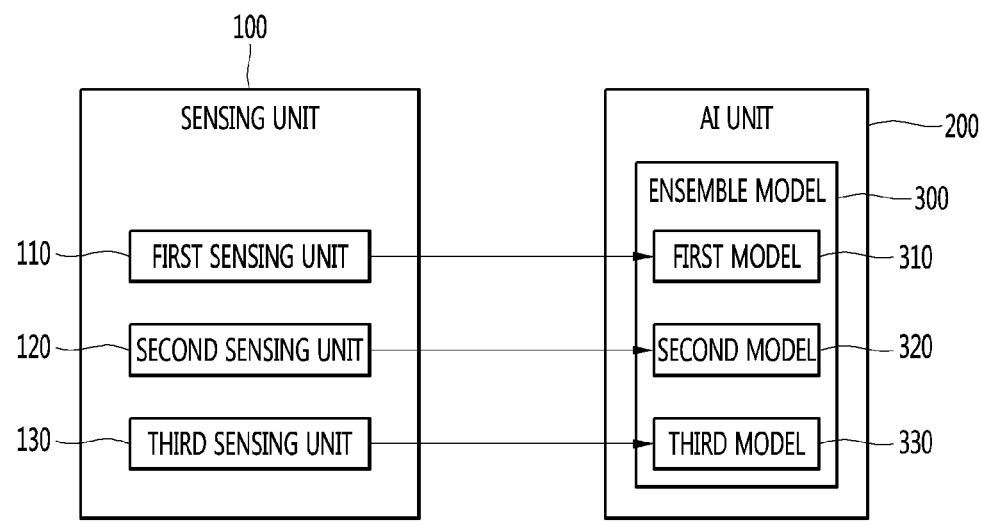
FIG. 2 is a block diagram for describing an artificial intelligence (AI) device according to an embodiment of the present invention.

FIG. 2 is a block diagram for describing an artificial intelligence (AI) device 10 according to an embodiment of the present invention.

The AI device 10 according to an embodiment of the present invention may include a sensing unit 100 and an AI unit 200.

The sensing unit 100 may obtain pieces of sensing information associated with a biometric state, for predicting the biometric state of a user.

In detail, a first sensing unit 110 of the sensing unit 100 may obtain first sensing information. Here, the first sensing information may be information obtained by sensing a motion of the user.

A second sensing unit 120 of the sensing unit 100 may obtain second sensing information. Here, the second sensing information may be information obtained by sensing a physiological signal of the user. Here, the physiological signal of the user may include at least one of a heart rate, a respiration rate, a respiration flow, and a temperature.

A third sensing unit 130 of the sensing unit 100 may obtain third sensing information. Here, the third sensing information may be information obtained by sensing a sound of the user. Here, the sound of the user may include at least one of snoring, a breathing sound, and a heartbeat sound of the user.

The AI unit 200 may include an ensemble model 300.

Here, the ensemble model may include a first model 310, a second model 320, and a third model 330.

Here, the first model 310 may be a model for predicting a motion state of the user by using the first sensing information and may be referred to as a motion prediction model.

The second model 320 may be a model for predicting a physiological state of the user by using the second sensing information and may be referred to as a physiological state prediction model.

The third model 330 may be a model for predicting a sound state of the user by using the third sensing information and may be referred to as a sound state prediction model.

The sensing unit 100 may transmit pieces of sensing information to the AI unit 200.

The AI unit 200 may input each of the pieces of sensing information to the ensemble model 300 as an input value.

In detail, the AI unit 200 may input the first sensing information to the first model 310. Also, the AI unit 200 may input the second sensing information to the second model 320. Also, the AI unit 200 may input the third sensing information to the third model 330.

The first model may output a first result value corresponding to the first sensing information input thereto. Here, the first result value output from the first model may denote a motion state of the user which is predicted based on the first sensing information by the first model.

The first model may be a machine learning model which is previously learned so as to output a result value corresponding to the first sensing information.

In this case, the first model may be a model which has trained an artificial neural network through supervised learning. For example, the first model may be a model which has been trained by inputting motion data of the user and a label (a motion state) corresponding to the motion data.

The second model may output a second result value corresponding to the second sensing information input thereto. Here, the second result value output from the second model may denote a motion state of the user which is predicted based on the second sensing information by the second model.

The second model may be a machine learning model which is previously learned so as to output a result value corresponding to the second sensing information.

In this case, the second model may be a model which has trained the artificial neural network through supervised learning. For example, the second model may be a model which is trained by inputting physiological data of the user and a label (a physiological state) corresponding to the physiological data.

The third model may output a third result value corresponding to the third sensing information input thereto. Here, the third result value output from the third model may denote a motion state of the user which is predicted based on the third sensing information by the third model.

The third model may be a machine learning model which is previously learned so as to output a result value corresponding to the third sensing information.

In this case, the third model may be a model which has trained the artificial neural network through supervised learning. For example, the third model may be a model which is trained by inputting sound data of the user and a label (a sound state) corresponding to the sound data.

The ensemble model 300 may combine the first result value output from the first model, the second result value output from the second model, and the third result value output from the third model to output a final result value.

For example, the ensemble model 300 may combine the motion state output from the first model, the physiological state output from the second model, and the sound state output from the third model to output information about a sleeping stage of the user.

In this case, the AI unit 200 may perform an operation corresponding to a biometric state of the user, based on the final result value.

For example, when the AI device 10 is an AI speaker, the AI unit 200 may control volume or may turn off the AI device 10, based on the sleeping stage of the user.

As another example, when the AI device 10 is an AI lighting device, the AI unit 200 may control illuminance, based on the sleeping stage of the user.

Figure 3:
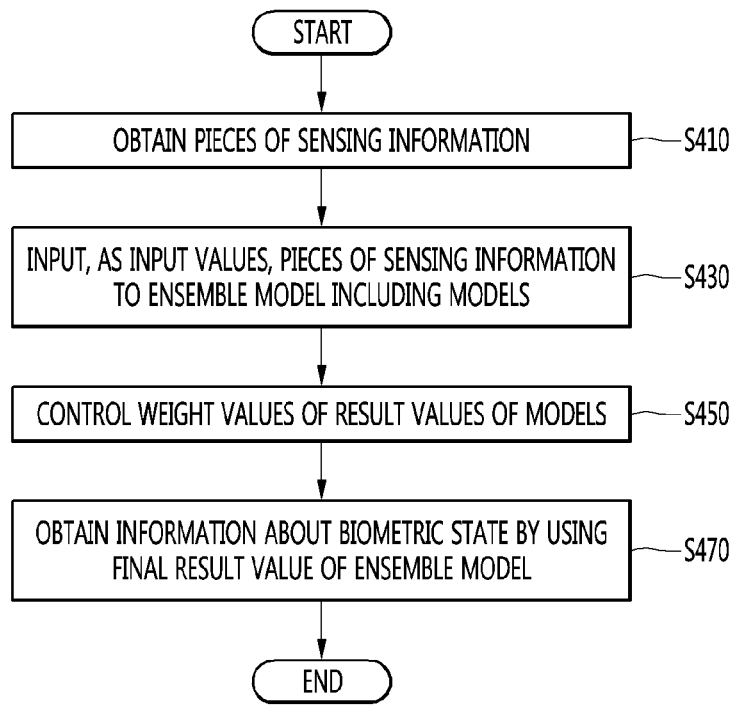
FIG. 3 is a flowchart for describing an operating method of an AI device according to an embodiment of the present invention.

FIG. 3 is a flowchart for describing an operating method of an AI device according to an embodiment of the present invention.

The operating method of the AI device according to an embodiment of the present invention may include step S410 of obtaining pieces of sensing information, step S430 of inputting, as input values, the pieces of sensing information to an ensemble model including a plurality of models, step S450 of determining weight values of result values of the plurality of models, based on at least one of the input values input to the plurality of models and result values output from the plurality of models, and step S470 of applying the weight values to the result values of the plurality of models to obtain a final result value and performing an operation corresponding to a biometric state, based on the final result value.

The above-described method may be for inputting the sensing information to the ensemble model to obtain a final result value and may be executed in a computer.

The AI device may obtain uncertainty by using at least one of an input value and a result value and may control weight values of result values of a plurality of models by using the uncertainty.

Figure 4:
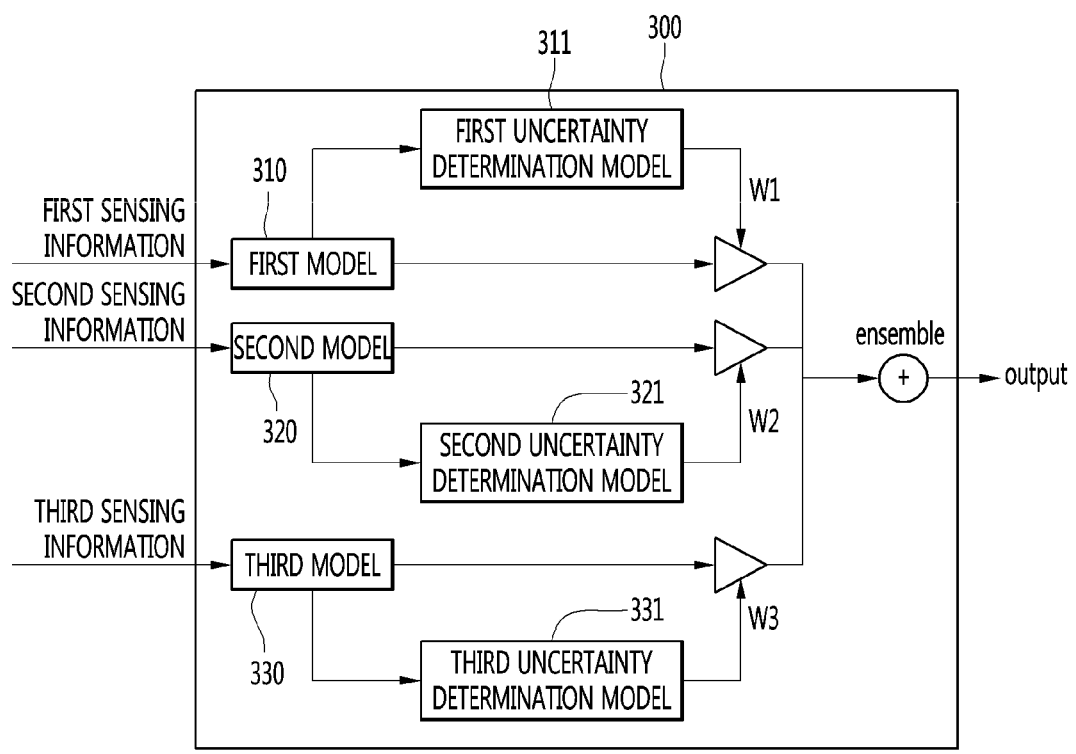
FIGS. 4 and 5 are diagrams for describing a weight value determining method according to a first embodiment of the present invention.
Figure 5:
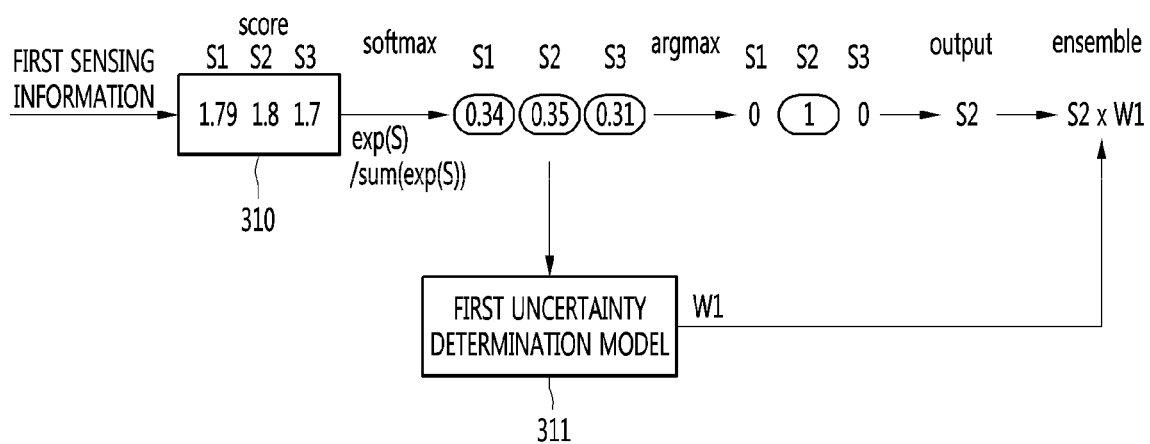

FIGS. 4 and 5 are diagrams for describing a weight value determining method according to a first embodiment of the present invention.

An AI unit may obtain weight values applied to result values output from a plurality of models (for example, first to third models) 310, 320, and 330, based on the result values output from the plurality of models 310, 320, and 330.

In detail, the first model 310 may output a plurality of probability values respectively corresponding to a plurality of classes. In this case, the AI unit may obtain an uncertainty of a first result value of the first model 310, based on a variance between the plurality of probability values.

In detail, referring to FIG. 5, when first sensing information is input, the first model 310 may obtain a plurality of scores "1.79, 1.8, and 1.7" respectively corresponding to a plurality of classes (for example, first to third classes) S1 to S3. Here, the plurality of classes S1 to S3 may be right answers which are to be predicted by the first model 310, and may respectively represent a plurality of motion states.

Moreover, the first model 310 may obtain a plurality of probability values "0.34, 0.35, and 0.31" respectively corresponding to the plurality of scores "1.79, 1.8, and 1.7".

The AI unit may include a first uncertainty determination model 311. Also, the first uncertainty determination model 311 may obtain a weight value W1 of a result value S2 of the first model 310 by using a variance between the plurality of probability values "0.34, 0.35, and 0.31".

In detail, it may be assumed that the first class S1 is a motion of a breast when a user breathes, the second class S2 is a motion where the user tosses and turns to the left, and the third class S3 is a motion where the user turns a body. Also, when first sensing information is information obtained by sensing a motion where the user tosses and turns to the left, a probability corresponding to the second class S2 may be output as a very high value, and for example, may be output as a probability value close to 1.

In this case, each of a probability value corresponding to the first class S1 and a probability value corresponding to the third class S3 may be output as a very low value, and for example, may be output as a probability value close to 0.

In this case, a variance between a plurality of probability values may be large. Also, when the variance between the plurality of probability values is large, the first uncertainty determination model 311 may determine an uncertainty of a first result value S2 of the first model 310 as a low level.

As another example, it may be assumed that the first class S1 is a motion of the breast when the user breathes, the second class S2 is a motion where the user tosses and turns to the left, and the third class S3 is a motion where the user turns the body. Also, it may be assumed that the first sensing information is noise (a motion where the user goes to a restroom).

When the first sensing information is the noise, data differing from a right answer which is to be predicted by the first model may be input, and thus, the variance between the plurality of probability values "0.34, 0.35, and 0.31" may be reduced. Also, when the variance between the plurality of probability values "0.34, 0.35, and 0.31" is small, the first uncertainty determination model 311 may determine the uncertainty of the first result value S2 of the first model 310 as a high level.

The first uncertainty determination model 311 may determine a first weight value W1 of the first result value S2, based on the uncertainty of the first result value S2.

The first model may output a result value corresponding to the first sensing information. In detail, the first model may output, as a result value, the class S2 where a score is largest or a probability value is largest.

An ensemble model 300 may apply (S2*W1) the first weight value W1 to the result value S2 of the first model.

The same process may be performed on the second model and the third model.

In detail, the AI unit may include a second uncertainty determination model 321. Also, the second uncertainty determination model 321 may obtain an uncertainty of a result value of the second model 320, based on a variance between a plurality of probability values output from the second model 320 and may determine a second weight value W2 of the result value of the second model.

Moreover, the AI unit may include a third uncertainty determination model 331. Also, the third uncertainty determination model 331 may obtain an uncertainty of a result value of the third model 330, based on a variance between a plurality of probability values output from the third model 330 and may determine a third weight value W3 of the result value of the third model.

The ensemble model 300 may apply the first weight value W1 to the first result value of the first model, the second weight value W2 to the second result value of the second model, and the third weight value W3 to the third result value of the third model.

Moreover, the ensemble model 300 may output a final output value by using the first result value with the first weight value applied thereto, the second result value with the second weight value applied thereto, and the third result value with the third weight value applied thereto.

Figure 6:
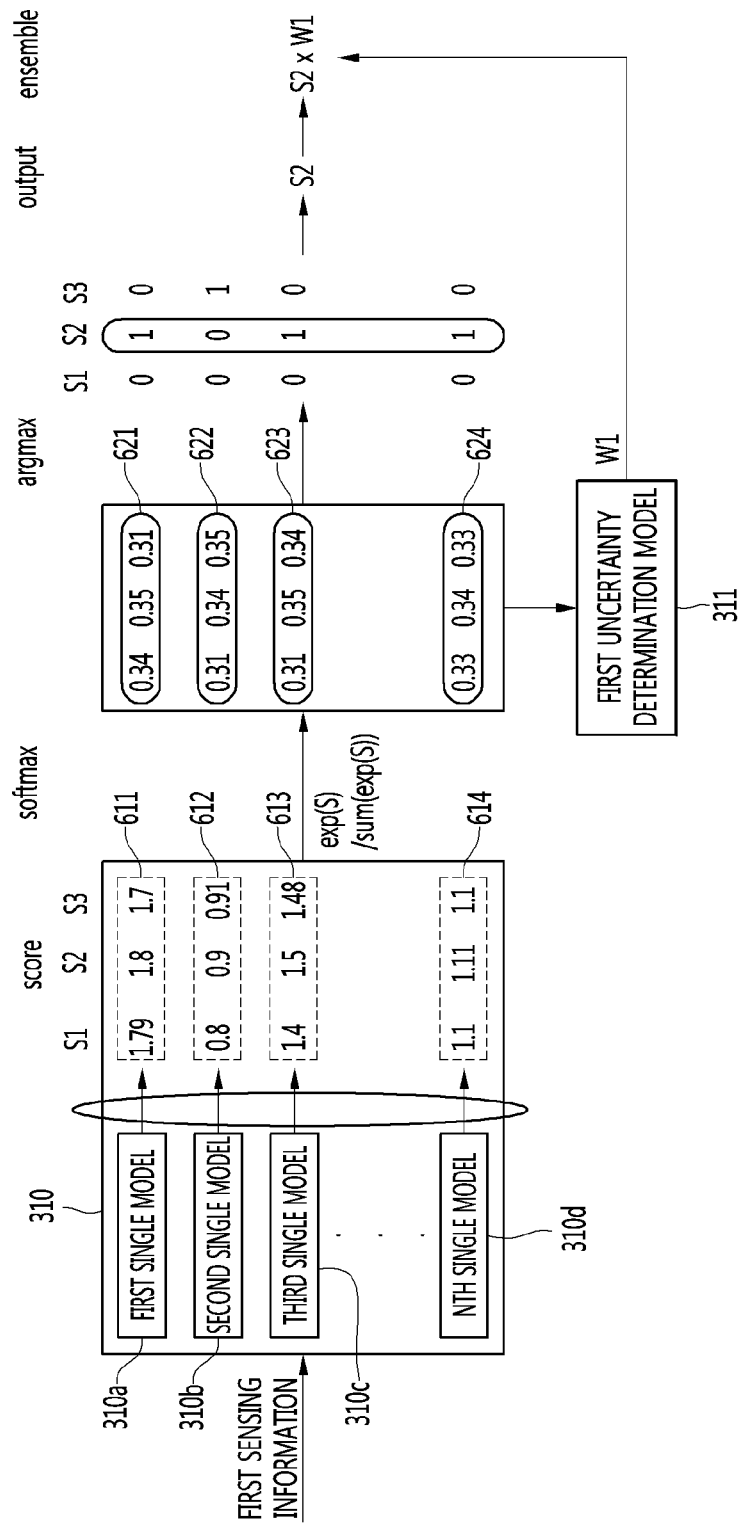
FIG. 6 is a diagram for describing a weight value determining method according to a second embodiment of the present invention.

FIG. 6 is a diagram for describing a weight value determining method according to a second embodiment of the present invention.

Hereinafter, the weight value determining method according to a second embodiment of the present invention will be described with reference to FIGS. 4 and 6.

A first model 310 may include one ensemble model including a plurality of single models 310a to 310d.

An AI unit may obtain a plurality of probability value sets (for example, first to fourth probability value sets) 621 to 624 which are obtained by randomly combining the plurality of single models 310a to 310d with respect to one input value.

In detail, when first sensing information is input, the first model 310 may randomly combine the plurality of single models 310a to 310d to output a plurality of score sets 611 to 614. Also, the first model 310 may output the plurality of probability value sets 621 to 624 respectively corresponding to the plurality of score sets 611 to 614.

In this case, the AI unit may obtain an uncertainty of a first result value of the first model, based on a variance between the plurality of probability value sets 621 to 624 which are output by randomly combining the plurality of single models 310a to 310d.

Moreover, the AI unit may obtain a weight value W1 of a result value S2 of the first model, based on the uncertainty of the first result value.

For example, the first probability value set 621 may be a probability value set corresponding to the score set 611 which is output by combining result values of a first single model, a second single model, and an $n^{th}$ single model.

As another example, the second probability value set 622 may be a probability value set corresponding to the score set 612 which is output by combining result values of the first single model, a third single model, and the $n^{th}$ single model.

When the first sensing information is data which is previously learned in the plurality of single models 310a to 310d, a variance between the plurality of probability value sets 621 to 624.

When the variance between the plurality of probability value sets 621 to 624 is small, the first uncertainty determination model 311 may determine an uncertainty of a first result value S2 of the first model as a low level.

On the other hand, when the first sensing information is noise instead of the data which is previously learned in the plurality of single models 310a to 310d, the variance between the plurality of probability value sets 621 to 624 may be large.

Moreover, when the variance between the plurality of probability value sets 621 to 624 is large, the first uncertainty determination model 311 may determine the uncertainty of the first result value S2 of the first model as a high level.

The first uncertainty determination model 311 may determine a first weight value W1 of the first result value S2, based on the uncertainty of the first result value S2.

In detail, when the uncertainty of the first result value S2 is a low level, the first uncertainty determination model 311 may determine a weight value W1 corresponding to a high level.

Moreover, when the uncertainty of the first result value S2 is a high level, the first uncertainty determination model 311 may determine a weight value W1 corresponding to a low level.

The first model may output a result value corresponding to the first sensing information. In detail, the first model may output, as a result value, the class S2 where a score is largest or a probability value is largest.

An ensemble model 300 may apply (S2*W1) the first weight value W1 to the result value S2 of the first model.

The same process may be performed on the second model and the third model.

For example, the second model 320 may be an ensemble model including a plurality of single models. Also, when second sensing information is input, the second model 320 may randomly combine the plurality of single models to output a plurality of probability value sets.

In this case, the AI unit may obtain an uncertainty of a second result value of the second model, based on a variance between a plurality of probability value sets which are output by randomly combining a plurality of single models.

Moreover, the AI unit may obtain a weight value of a result value of the second model, based on the uncertainty of the second result value.

The ensemble model 300 may apply the first weight value W1 to the first result value of the first model, the second weight value W2 to the second result value of the second model, and the third weight value W3 to a third result value of the third model.

Moreover, the ensemble model 300 may output a final output value by using the first result value with the first weight value applied thereto, the second result value with the second weight value applied thereto, and the third result value with the third weight value applied thereto.

Figure 7:
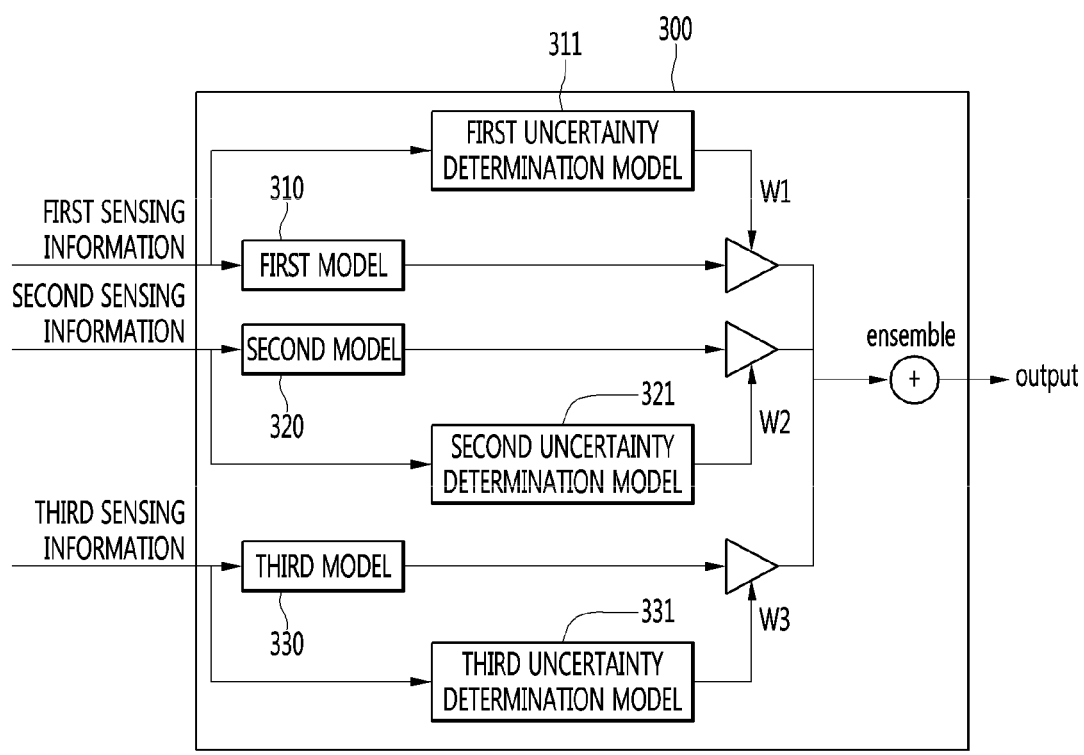
FIGS. 7 and 8 are diagrams for describing a weight value determining method according to a third embodiment of the present invention.
Figure 8:
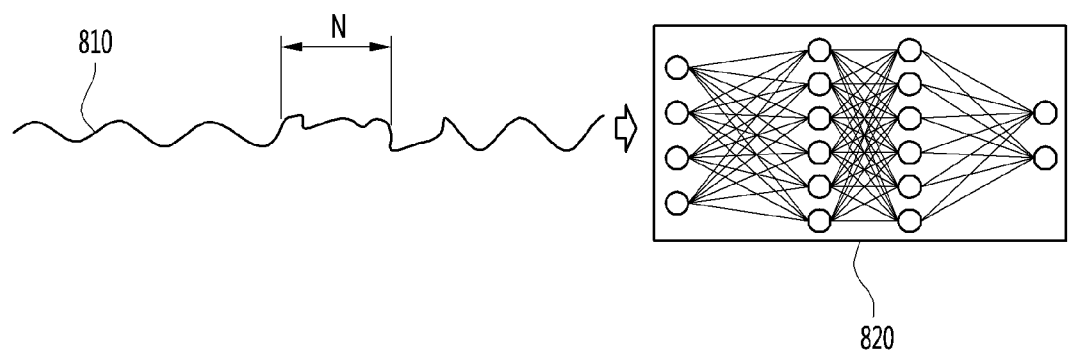

FIGS. 7 and 8 are diagrams for describing a weight value determining method according to a third embodiment of the present invention.

An AI unit 300 may obtain a weight value applied to result values output from a plurality of models (for example, first to third models) 310, 320, and 330, based on sensing information input to the plurality of models 310, 320, and 330.

In detail, first sensing information may be input to the first model. In this case, the first sensing information may be input to a first uncertainty determination model 311. Here, the first uncertainty determination model 311 may be a machine learning model 820 pre-learning noise of the first sensing information.

In detail, referring to FIG. 8, the first uncertainty determination model 311 may be the machine learning model 820 which has been trained by inputting noise data N and an uncertainty corresponding to the noise data N.

For example, the first uncertainty determination model 311 may be a machine learning model which has been trained by inputting sensing information 810, sensed when a user goes to a restroom, and an uncertainty corresponding to the sensing information.

When first sensing information is input to the first uncertainty determination model 311, the first uncertainty determination model 311 may output an uncertainty corresponding to the first sensing information.

Moreover, the AI unit 300 may determine a weight value of a result value of a first model, based on an uncertainty output from the first uncertainty determination model 311.

The same process may be performed in the second model and the third model.

For example, when second sensing information is input to a second uncertainty determination model 321, the second uncertainty determination model 321 may output an uncertainty corresponding to the second sensing information. In this case, the AI unit 300 may determine a weight value of a result value of the second model, based on an uncertainty output from the second uncertainty determination model 321.

Moreover, when third sensing information is input to a third uncertainty determination model 331, the third uncertainty determination model 331 may output an uncertainty corresponding to the third sensing information. In this case, the AI unit 300 may determine a weight value of a result value of the third model, based on an uncertainty output from the third uncertainty determination model 331.

The ensemble model 300 may apply a first weight value W1 to a first result value of the first model, a second weight value W2 to a second result value of the second model, and a third weight value W3 to a third result value of the third model.

Moreover, the ensemble model 300 may output a final output value by using the first result value with the first weight value applied thereto, the second result value with the second weight value applied thereto, and the third result value with the third weight value applied thereto.

Figure 9:
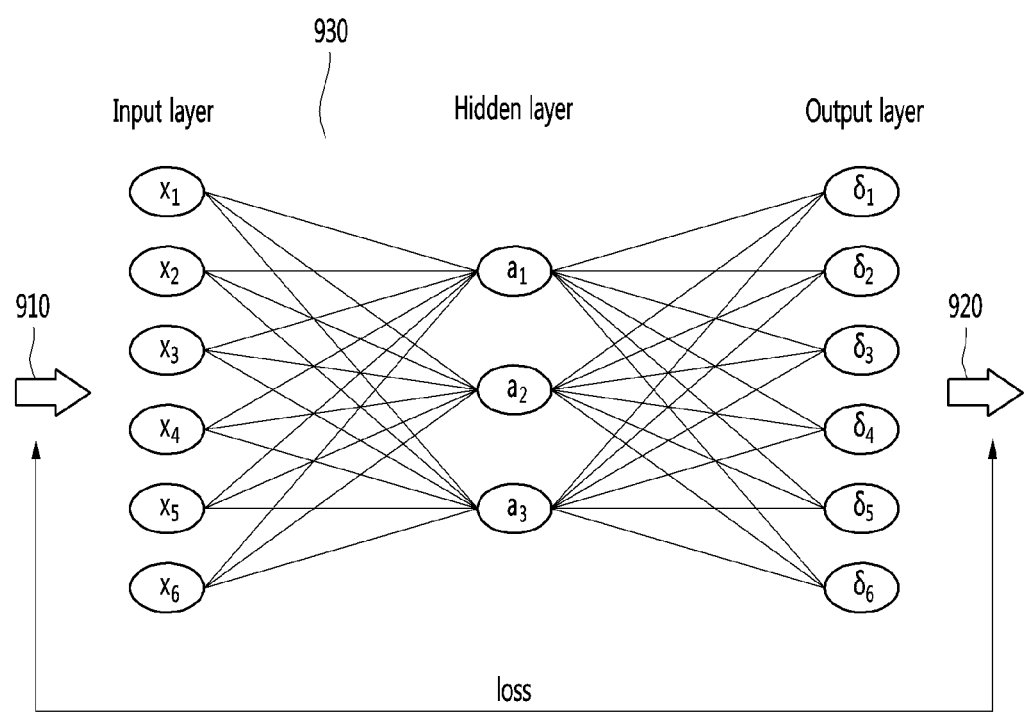
FIG. 9 is a diagram for describing a weight value determining method according to a fourth embodiment of the present invention.

FIG. 9 is a diagram for describing a weight value determining method according to a fourth embodiment of the present invention.

An AI unit may obtain weight values applied to result values output from a plurality of models (for example, first to third models) 310, 320, and 330, based on sensing information input to the plurality of models 310, 320, and 330.

First sensing information may be input to the first model. In this case, the first sensing information may be input to a first uncertainty determination model 311. Here, the first uncertainty determination model 311 may be an auto encoder pre-learning a plurality of classes of the first model.

In detail, when a first class S1 is a motion of a breast when a user breathes, a second class S2 is a motion where the user tosses and turns to the left, and a third class S3 is a motion where the user turns a body, sensing information corresponding to the first class S1, sensing information corresponding to the second class S2, and sensing information corresponding to the third class S3 may be provided as learning data and output data to an auto encoder 930. Also, the auto encoder 930 may be trained to minimize a loss of each of the learning data and the output data.

When first sensing information 910 is input to the auto encoder 930, the auto encoder may output a result value 920 corresponding to the first sensing information 910 input thereto.

In this case, a first uncertainty determination model 311 may obtain an uncertainty of a result value of the first model, based on a loss of each of the first sensing information input to the auto encoder and the result value output from the auto encoder.

In terms of a characteristic of the auto encoder, the auto encoder may output a result value which enables an input value to be almost identically restored, with respect to data similar to learned data, but when data differing from learned data is input, the auto encoder cannot normally perform a restoration operation.

For example, when the first sensing information 910 is data obtained by sensing the first class S1, the loss of each of the first sensing information input to the auto encoder and the result value output from the auto encoder may be small. Also, when the loss is small, an uncertainty of the result value of the first model may be a low level.

Moreover, when the uncertainty of the result value of the first model is a low level, the AI unit may output a weight value corresponding to a high level.

As another example, when the first sensing information 910 is noise, the loss of each of the first sensing information input to the auto encoder and the result value output from the auto encoder may be large. Also, when the loss is large, the uncertainty of the result value of the first model may be a high level.

Moreover, when the uncertainty of the result value of the first model is a high level, the AI unit may output a weight value corresponding to a low level.

The same process may be performed in the second model and the third model.

The ensemble model 300 may apply a first weight value W1 to a first result value of the first model, a second weight value W2 to a second result value of the second model, and a third weight value W3 to a third result value of the third model.

Moreover, the ensemble model 300 may output a final output value by using the first result value with the first weight value applied thereto, the second result value with the second weight value applied thereto, and the third result value with the third weight value applied thereto.

Figure 10:
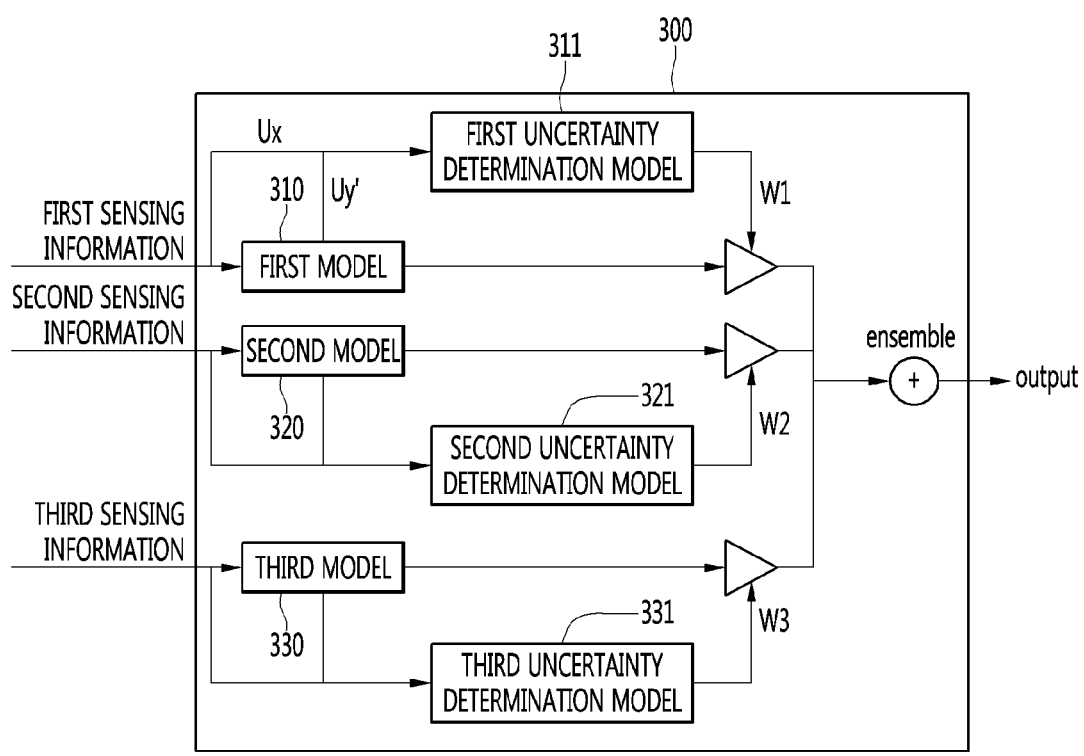
FIG. 10 is a diagram for describing a weight value determining method according to a fifth embodiment of the present invention.

FIG. 10 is a diagram for describing a weight value determining method according to a fifth embodiment of the present invention.

An AI unit may obtain weight values applied to result values output from a plurality of models (for example, first to third models) 310, 320, and 330, based on sensing information input to the plurality of models 310, 320, and 330 and the result values output from the plurality of models 310, 320, and 330.

In detail, a first uncertainty determination model may obtain a $1\text{-}1^{th}$ uncertainty Ux by using first sensing information input to the first model. Also, the first uncertainty determination model may obtain a $1\text{-}2^{th}$ uncertainty Uy' by using an output value output from the first model.

In this case, the first uncertainty determination model may obtain an uncertainty of a result value of the first model by using the $1\text{-}1^{th}$ uncertainty Ux and the $1\text{-}2^{th}$ uncertainty Uy' and may obtain a first weight value W1 applied to a result value of the first model.

The same process may be performed in the second model and the third model.

The ensemble model 300 may apply a first weight value W1 to a first result value of the first model, a second weight value W2 to a second result value of the second model, and a third weight value W3 to a third result value of the third model.

Moreover, the ensemble model 300 may output a final output value by using the first result value with the first weight value applied thereto, the second result value with the second weight value applied thereto, and the third result value with the third weight value applied thereto.

The AI unit may include a weight determination model (not shown). Also, the weight determination model (not shown) may output weight values W1 to W3 corresponding to first sensing information, second sensing information, and third sensing information.

In detail, the weight determination model (not shown) may be a learning model pre-learning a weight value based on an uncertainty.

Figure 11:
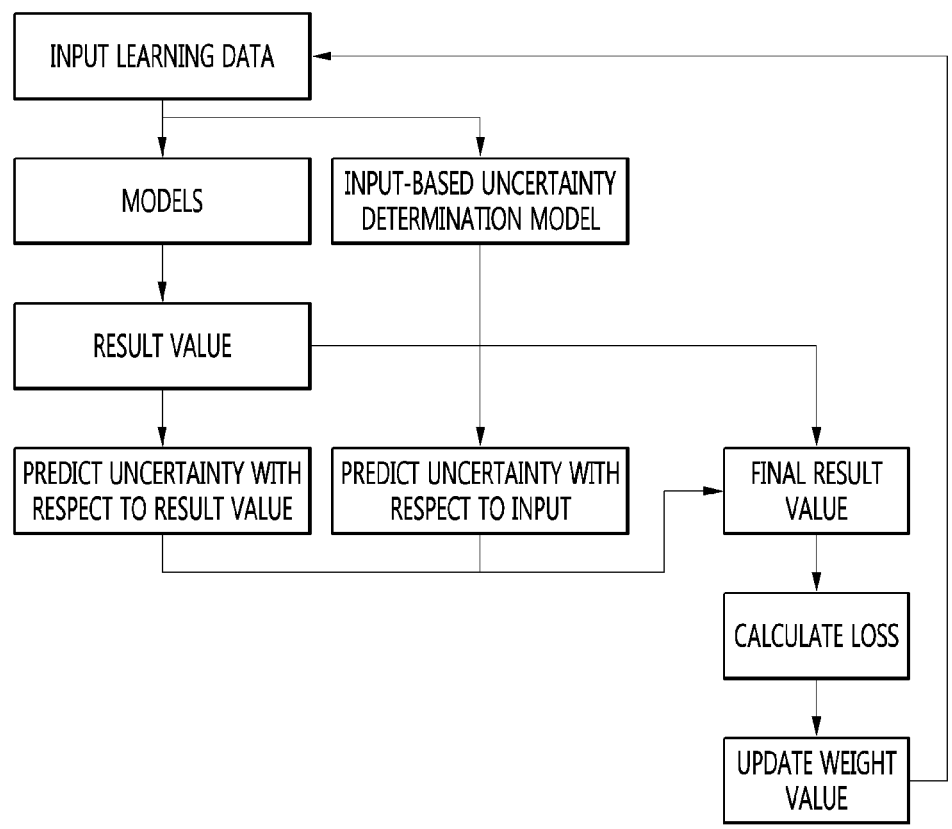
FIG. 11 is a diagram for describing a learning process of a weight determination model.

A learning process of the weight determination model will be described below with reference to FIG. 11.

Sensing data may be input as learning data. In this case, a plurality of models may output a result value corresponding to input data.

The sensing information may be input to an input-based uncertainty determination model, and the input-based uncertainty determination model may output an uncertainty Ux corresponding to sensing information.

Moreover, a result value output from each of the plurality of models may be input to a result value-based uncertainty determination model. In this case, the result value-based uncertainty determination model may output an uncertainty Uy' corresponding to a result value output from each of the plurality of models.

The ensemble model may combine the uncertainty Ux corresponding to the sensing information and the uncertainty Uy' corresponding to the result value to obtain a weight value ($\pi$(Ux, Uy')) and may obtain a final result value ($\pi$(Ux, Uy')F(x)) which is obtained by applying the obtained weight value to the result value.

The weight determination model may search for a weight value for minimizing a loss (L($\pi$(Ux, Uy')Fx, y)) between learning data and the final result value ($\pi$(Ux, Uy')F(x)) or minimizing an uncertainty.

This may be represented by the following Equation (1):

$$\text{ensemble loss:} L(vF(x),y) = \pi(Ux,Uy')F(x) \qquad (1)$$

The weight determination model may search for a, b, and c for minimizing a loss in the following Equation (2), or may search for a for minimizing a loss in the following Equation (3):

$$v = \pi(Ux, Uy') = aUx + bUy' + c \qquad (2)$$

$$v = \pi(Ux, Uy') = a(Ux + Uy') \qquad (3)$$

Moreover, by repeating such a process, the weight determination model may be learned to predict a weight value corresponding to the sensing information.

Figure 12:
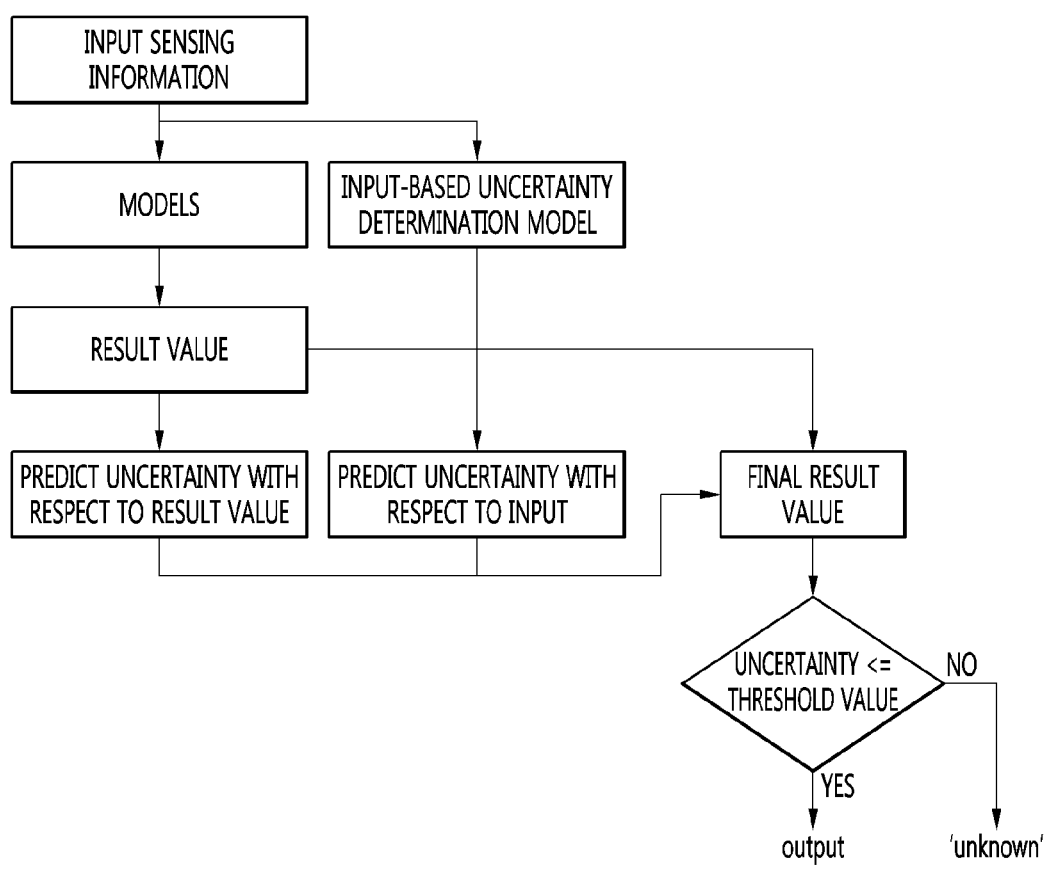
FIG. 12 is a diagram for describing a method of determining, by a weight determination model, a weight value corresponding to sensing information.

FIG. 12 is a diagram for describing a method of determining, by a weight determination model, a weight value corresponding to sensing information.

Sensing information may be input. In this case, each of a plurality of models may output a result value corresponding to input data.

The sensing information may be input to an input-based uncertainty determination model, and the input-based uncertainty determination model may output an uncertainty Ux corresponding to the sensing information.

Moreover, result values output from the plurality of models may be input to a result value-based uncertainty determination model. In this case, the result value-based uncertainty determination model may output an uncertainty Uy' corresponding to the result value output from each of the plurality of models.

A learned weight determination model may output a weight value ($\pi$(Ux, Uy')) by using the uncertainty Ux corresponding to the sensing information and the uncertainty Uy' corresponding to the result value.

In this case, an ensemble model may apply weight values to the result values of the plurality of models to output a final output value.

The ensemble model may output or may not output the final result value, based on the uncertainty.

For example, when the uncertainty is less than a threshold value, the ensemble model may output the final result value.

On the other hand, when the uncertainty is greater than the threshold value, the ensemble model may not output the final result value, or may output information representing that it is unable to search for a right answer.

Figure 13:
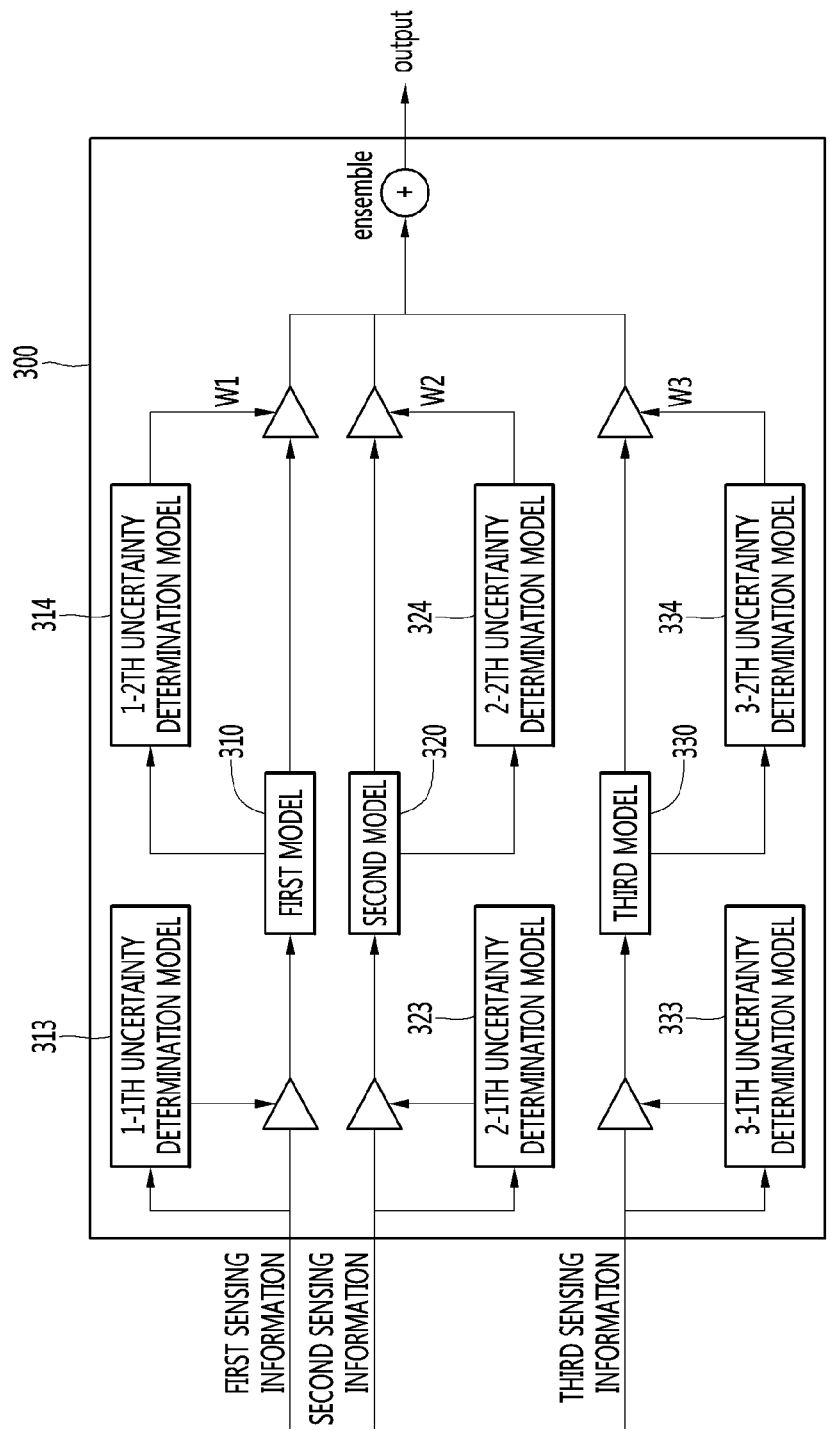
FIG. 13 is a diagram for describing a method of determining, by a weight determination model, a weight value corresponding to sensing information according to a sixth embodiment of the present invention.

FIG. 13 is a diagram for describing a weight value determining method according to a sixth embodiment of the present invention.

An AI unit may obtain weight values applied to result values output from a plurality of models (for example, first to third models) 310, 320, and 330, based on sensing information input to the plurality of models 310, 320, and 330 and the result values output from the plurality of models 310, 320, and 330.

In detail, a 1-1$^{th}$ uncertainty determination model 313 may obtain a 1-1$^{th}$ uncertainty by using first sensing information input to the first model.

The 1-1$^{th}$ uncertainty determination model 313 may determine whether the 1-1$^{th}$ uncertainty is lower than a predetermined value. Also, when the 1-1$^{th}$ uncertainty is lower than the predetermined value, the 1-1$^{th}$ uncertainty determination model 313 may input the first sensing information to the first model. On the other hand, when the 1-1$^{th}$ uncertainty is higher than the predetermined value, the 1-1$^{th}$ uncertainty determination model 313 may block an input of the first sensing information to the first model.

A 1-2$^{th}$ uncertainty determination model 314 may obtain a 1-2$^{th}$ uncertainty by using a result value output from the first model. Also, the 1-2$^{th}$ uncertainty determination model 314 may determine a first weight value W1 of a first result value S2, based on the 1-2$^{th}$ uncertainty.

The same process may be performed in the second model and the third model (e.g.c 323, 324, 333 and 334).

The present invention may obtain biometric information about a user by using an ensemble model configured by a combination of a motion model, a sound model, and a physiological model, thereby preventing performance from being reduced when low-quality sensing information is received.

Moreover, the present invention may calculate an uncertainty of a result value of each model to determine a quality of sensing information input to each model. Also, the present invention may reduce a weight value corresponding to an output value of a model to which low-quality sensing information is input and may increase a weight value corresponding to an output value of a model to which high-quality sensing information is input, thereby outputting a final result value having high reliability.

Moreover, when reliability is low, the present invention may not output a final result value, thereby preventing a risk caused by an output of an abnormal final result value.

Moreover, it has been described that the present invention is applied for determining a sleeping state a user, but the present invention is not limited thereto.

For example, the present invention may be applied to an apparatus which determines an optimal operation by using information collected through various sensors like self-driving vehicles.

The present invention mentioned in the foregoing description may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the mobile terminal.

The foregoing embodiments are merely exemplary and are not to be considered as limiting the present disclosure. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds, are therefore intended to be embraced by the appended claims.

What is claimed is:

1. A computer-implemented method for controlling a device based on an ensemble model, the computer-implemented method comprising:
receiving, via a plurality of sensors in the device, pieces of sensing information associated with a biometric state of a user;
inputting, by a processor of the device, first sensing information of the pieces of sensing information to a first model among a plurality of models in the ensemble model, determining a first uncertainty of the first model by directly inputting the first sensing information into a first uncertainty model and by directly inputting an output value of the first model into the first uncertainty model, and generating a first weight value for weighting a first result value of the first model based on the first uncertainty, the first result value corresponding to a motion state of the user or a sound state of the user;
inputting, by the processor, second sensing information of the pieces of sensing information to a second model among the plurality of models in the ensemble model, determining a second uncertainty of the second model by directly inputting the second sensing information into a second uncertainty model and by directly inputting an output value of the second model into the second uncertainty model, and generating a second weight value for weighting a second result value of the second model based on the second uncertainty, the second result value corresponding to a physiological state of the user;
generating, by the processor, a final result value based on combining the first result value weighted by the first weight value and the second result value weighted by the second weight value;
generating, by the processor, a predicted biometric state of the user based on the final result value; and
wherein the first weight value is different from the second weight value,
wherein the method further comprises:
in response to the predicted biometric state of the user corresponding to a sleeping state, executing at least one of turning off the device, reducing a volume of sound output by the device, or turning off or dimming a light of the device,
wherein the generating the first weight value comprises inputting the first sensing information to an auto encoder pre-learning a plurality of classes of the first model, and obtaining the first uncertainty, based on a loss between an input value and an output value of the auto encoder, and
wherein
the first model comprises a plurality of single models, and
the generating the first weight value comprises obtaining a plurality of probability value sets output by randomly combining the plurality of single models with respect to one input value, and obtaining the first uncertainty, based on a variance between the plurality of probability value sets.

2. The computer-implemented method of claim 1, wherein the generating the first weight value comprises inputting the first sensing information to a machine learning model pre-learning noise of the first sensing information, and obtaining the first uncertainty output from the machine learning model.

3. The computer-implemented method of claim 1, wherein the generating the first weight value comprises determining the first weight value of the first result value, based on both of the first sensing information input to the first model and the output value output from the first model.

4. The computer-implemented method of claim 1, wherein
the first sensing information is information obtained by sensing a motion of a user, and
the second sensing information is a physiological signal of the user.

5. The computer-implemented method of claim 1, wherein the second sensing information includes at least one of a heart rate signal of the user, a temperature of the user, or breathing sounds of the user.

6. An artificial intelligence (AI) device comprising:
a plurality of sensors configured to receive pieces of sensing information associated with a biometric state of a user; and
a processor configured to:
input first sensing information of the pieces of sensing information to a first model among a plurality of models in an ensemble model, determine a first uncertainty of the first model by directly inputting the first sensing information into a first uncertainty model and by directly inputting an output value of the first model into the first uncertainty model, and generate a first weight value for weighting a first result value of the first model based on the first uncertainty, the first result value corresponding to a motion state of the user or a sound state of the user,
input second sensing information of the pieces of sensing information to a second model among the plurality of models in the ensemble model, determine a second uncertainty of the second model by directly inputting the second sensing information into a second uncertainty model and by directly inputting an output value of the second model into the second uncertainty model, and generate a second weight value for weighting a second result value of the second model based on the second uncertainty, the second result value corresponding to a physiological state of the user,
generate a final result value based on combining the first result value weighted by the first weight value and the second result value weighted by the second weight value,
generate a predicted biometric state of the user based on the final result value, and
execute an operation of the device based on the predicted biometric state of the user,
wherein the first weight value is different from the second weight value,
wherein the processor is further configured to:
in response to the predicted biometric state of the user corresponding to a sleeping state, execute at least one of turning off the device, reducing a volume of sound output by the device, or turning off or dimming a light of the device, wherein the processor is further configured to input the first sensing information to an auto encoder pre-learning a plurality of classes of the first model, and obtain the first uncertainty, based on a loss between an input value and an output value of the auto encoder, and
wherein
the first model comprises a plurality of single models, and
the processor obtains a plurality of probability value sets output by randomly combining the plurality of single models with respect to one input value, and obtains the first uncertainty, based on a variance between the plurality of probability value sets.

7. The AI device of claim 6, wherein the processor is further configured to input the first sensing information to a machine learning model pre-learning noise of the first sensing information, and obtain the first uncertainty output from the machine learning model.

8. The AI device of claim 6, wherein the processor is further configured to generate the first weight value of the first result value, based on both of the first sensing information input to the first model and the value output from the first model.

9. The AI device of claim 6, wherein
the first sensing information is information obtained by sensing a motion of a user, and
the second sensing information is a physiological signal of the user.

10. The AI device of claim 6, wherein the second sensing information includes at least one of a heart rate signal of the user, a temperature of the user, or breathing sounds of the user.

* * * * *